(12) United States Patent
Nanaumi et al.

(10) Patent No.: US 10,690,587 B2
(45) Date of Patent: Jun. 23, 2020

(54) ACOUSTIC PROBE AND ACOUSTIC APPARATUS

(71) Applicant: CANON KABUSHIKI KAISHA, Tokyo (JP)

(72) Inventors: Ryuichi Nanaumi, Tokyo (JP); Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 16/018,688

(22) Filed: Jun. 26, 2018

(65) Prior Publication Data

US 2019/0003958 A1 Jan. 3, 2019

(30) Foreign Application Priority Data

Jun. 30, 2017 (JP) .................. 2017-129593

(51) Int. Cl.
*G01N 21/17* (2006.01)
*A61B 5/00* (2006.01)

(52) U.S. Cl.
CPC ....... *G01N 21/1702* (2013.01); *A61B 5/0095* (2013.01); *G01N 2021/1706* (2013.01); *G01N 2021/1708* (2013.01)

(58) Field of Classification Search
CPC ............. A61B 5/0095; G01N 21/1702; G01N 2021/1708; G01N 2021/1706
USPC .......................................................... 73/601
See application file for complete search history.

(56) References Cited

U.S. PATENT DOCUMENTS 5,974,898 A * 11/1999 Golderer ................. G01L 1/142
73/862.043
5,987,991 A * 11/1999 Trantow ............. G01N 29/2418
73/624
6,216,025 B1 4/2001 Kruger
2015/0334308 A1* 11/2015 Abe ......................... G06K 9/46
348/77
2016/0150973 A1* 6/2016 Abe ..................... A61B 5/0095
600/409

FOREIGN PATENT DOCUMENTS

WO WO2010030817 A1 * 3/2010

OTHER PUBLICATIONS

X. Luis Dean-Ben, Daniel Razansky; Portable spherical array probe for volumetric real-time optoacoustic imaging at centimeter-scale depths; Optics Express; Nov. 8, 2013; pp. 28062-28071; vol. 21; No. 23; The Optical Society (OSA); USA.

* cited by examiner

*Primary Examiner* — Jacques M Saint Surin
(74) *Attorney, Agent, or Firm* — Canon U.S.A., Inc. I.P. Division

(57) ABSTRACT

An acoustic probe includes a plurality of transducers that receives acoustic waves and a supporting body including a supporting portion having a symmetrical concave surface, such as a spherical cap surface, which supports the transducers in a spiral array. The supporting position R at which the supporting portion supports the transducers is given as $R(r_0, \theta, \varphi)$ [m, rad, rad] by a polar coordinate with respect to a center of the symmetrical concave surface by setting a sphere radius, a zenith angle, and an azimuth angle as "$r_0$", "$\theta$", and "$\varphi$", wherein the plurality of transducers is arrayed at a set azimuth angle spiral pitch in an azimuth angle direction and an axis direction spiral pitch set parallel to a central axis direction of the symmetrical concave surface, and wherein the azimuth angle spiral pitch is an angle acquired by dividing $2\pi$ by 1+golden number.

28 Claims, 6 Drawing Sheets

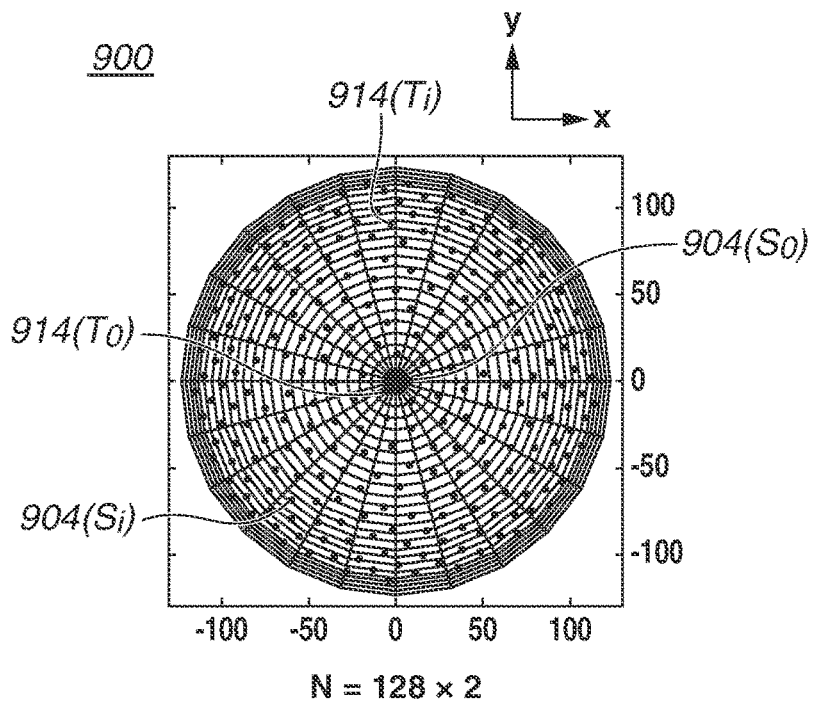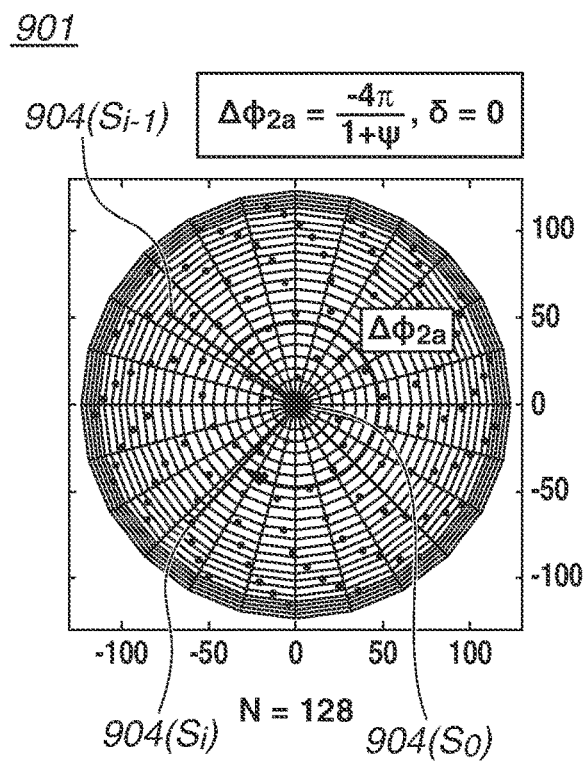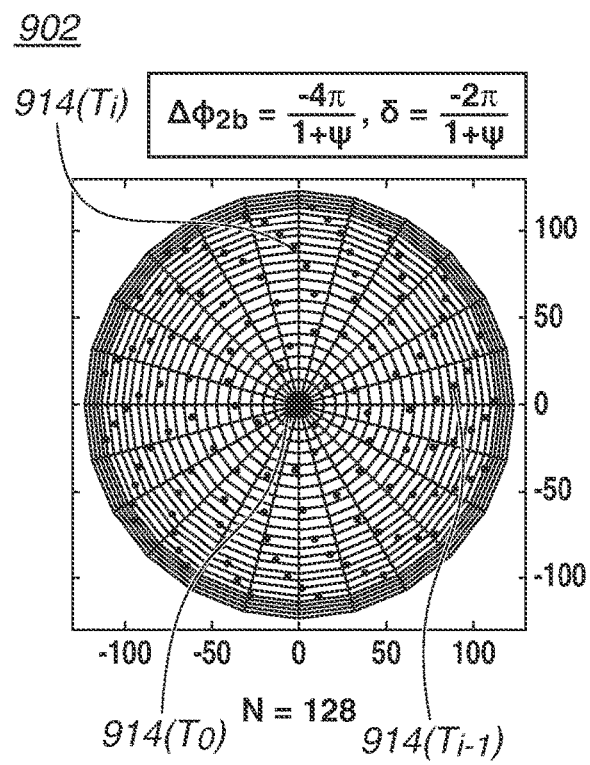

ACOUSTIC PROBE AND ACOUSTIC APPARATUS

BACKGROUND OF THE INVENTION

Field of the Invention

The present invention relates to an acoustic probe that receives an acoustic wave.

Description of the Related Art

There is provided an acoustic apparatus such as a photoacoustic imaging apparatus or an ultrasonic-echo imaging apparatus as a technique for receiving an acoustic wave and acquiring information about an interior of a test subject of a living subject.

An optoacoustic imaging apparatus for acquiring a cross-sectional image, which includes a light source for emitting infrared light and an acoustic probe, is described in a non-patent literature 1, "Portable spherical array probe for volumetric real-time optoacoustic imaging at centimeter-scale depths, OPTICS EXPRESS Vol. 21, No. 23, 28062 (2013)". Further, according to the technique described in the non-patent literature 1, artifacts arising in a reconstructed image can be reduced by receiving an acoustic wave transmitted from a region of interest (ROI) at a wide solid angle by forming the acoustic probe into a spherical array-shape.

A thermoacoustic imaging apparatus having a microwave source and an acoustic probe, which acquires a cross-sectional image is discussed in a specification of U.S. Pat. No. 6,216,025. In U.S. Pat. No. 6,216,025, transducers are uniformly and spirally arranged in an azimuth angle direction and a spiral-center axis direction of a spherical array-shaped acoustic probe.

In the acoustic probe described in the non-patent literature 1, since uniform-dispersibility arrangement of transducers is not taken into consideration, deviation arises in the mounting density of the transducers, which generates the artifacts in the reconstructed image. Therefore, there is a case where image quality of an acquired reconstructed image is reduced.

In the acoustic probe described in U.S. Pat. No. 6,216,025, dispersibility in the azimuth angle direction is not sufficient although uniform-dispersibility arrangement of transducers is taken into consideration, and thus image quality of the acquired reconstructed image may be reduced.

SUMMARY OF THE INVENTION

In consideration of the above-described problems, the present invention features an acoustic probe having high uniform dispersibility of transducers in both of the azimuth angle direction and the spiral center axis direction, which is capable of acquiring a reconstructed image with reduced artifacts.

According to an aspect of the present invention, an acoustic probe includes a plurality of transducers that receives acoustic waves and a supporting body including a supporting portion having a spherical surface which supports the plurality of transducers to form a spiral array, wherein a supporting position R at which the supporting portion supports the transducers is defined as $R(r_0, \theta, \varphi)$ [m, rad, rad] by a polar coordinate with respect to a center of the spherical surface by setting a sphere radius, a zenith angle, and an azimuth angle as "$r_0$", "$\theta$", and "$\varphi$", wherein the plurality of transducers is arrayed at a certain azimuth angle spiral pitch in an azimuth angle direction and a certain axis direction spiral pitch that is parallel to a central axis direction extending from the center to an extreme point, and wherein the azimuth angle spiral pitch is an angle [rad] acquired by dividing $2\pi$ [rad] by 1+golden number.

According to another aspect of the present invention, an acoustic probe includes a plurality of transducers that receives acoustic waves and a supporting body including a supporting portion having a spherical surface which supports the transducers, wherein a supporting position R at which the supporting portion supports the transducers is defined as $R(r_0, \theta, \varphi)$ [m, rad, rad] by a polar coordinate with respect to a center of the spherical surface by setting a sphere radius, a zenith angle, and an azimuth angle as "$r_0$", "$\theta$", and "$\varphi$", wherein the supporting portion supports the transducers in a spiral array that satisfies the following general expressions 1, 2, and 3.

$$\Delta\phi = \phi_i - \phi_{i-1} = \frac{\pm 2\pi}{1+\Psi} \tag{1}$$

$$\Psi = \frac{1+\sqrt{5}}{2} \tag{2}$$

$$\Delta z = z_i - z_{i-1} = r_0(\cos\theta_i - \cos\theta_{i-1}) = r_0 \frac{\cos\theta_{N-1} - \cos\theta_0}{N-1} \tag{3}$$

wherein "N" represents a number of transducers, represents an array number (0, 1, ..., N–1) assigned from 0 to each transducer by designating a side having "$\pi$" of the zenith angle $\theta$ as a starting point.

According to yet another aspect of the present invention, an acoustic probe includes a plurality of transducers that receives acoustic waves and a supporting body including a supporting portion having a spherical surface which supports the transducers, wherein a supporting position R at which the supporting portion supports the transducers is defined as $R(r_0, \theta, \varphi)$ [m, rad, rad] by a polar coordinate with respect to a center of the spherical surface by setting a sphere radius, a zenith angle, and an azimuth angle as "$r_0$", "$\theta$", and "$\varphi$", wherein the supporting portion supports the transducers in a spiral array that satisfies the following general expressions 4, 2, and 5.

$$\phi_i = \frac{\pm 2\pi i}{1+\Psi} \tag{4}$$

$$\Psi = \frac{1+\sqrt{5}}{2} \tag{2}$$

$$\theta_i = \cos^{-1}\left[\cos\theta_0 + \frac{\cos\theta_{N-1} - \cos\theta_0}{N-1}i\right] \tag{5}$$

wherein "N" represents a number of transducers, "i" represents an array number (0, 1, ..., N–1) assigned from 0 to each transducer by designating a side having "$\pi$" of the zenith angle $\theta$ as a starting point.

$$\Delta z = z_i - z_{i-1} = r_0(\cos\theta_i - \cos\theta_{i-1}) = r_0 \frac{\cos\theta_{N-1} - \cos\theta_0}{N-1} \tag{3}$$

Further features of the present invention will become apparent from the following description of exemplary embodiments with reference to the attached drawings.

BRIEF DESCRIPTION OF THE DRAWINGS

FIGS. 2A, 2B, and 2C are a bird's-eye views illustrating an acoustic probe according to a reference embodiment and spiral arrays which constitute the acoustic probe.

DESCRIPTION OF THE EMBODIMENTS

Figure 1A:
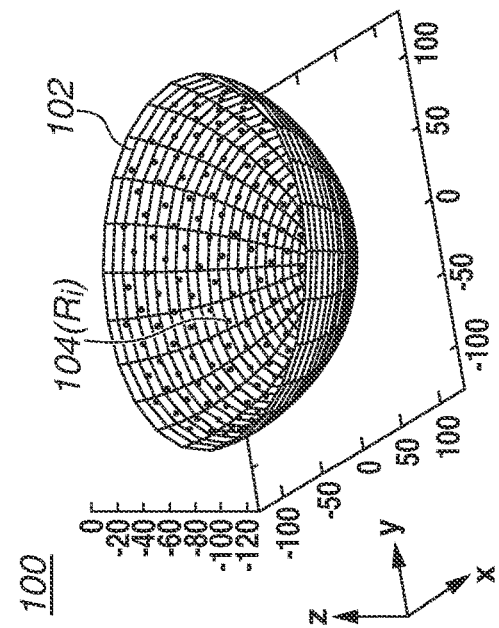
FIGS. 1A, 1B, 1C, and 1D are a cross-sectional schematic view, a bird's-eye view, a polar coordination, and a plan view illustrating arrangement of transducers of an acoustic probe according to a first exemplary embodiment.
Figure 1B:
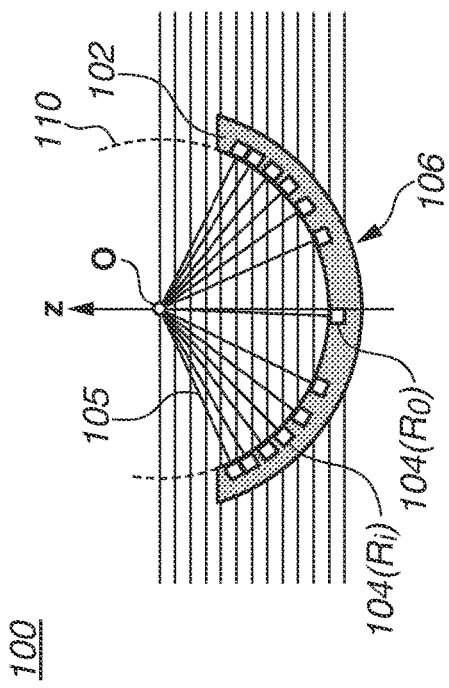

Hereinafter, exemplary embodiments of the present invention will be described in detail with reference to the appended drawings. In principle, the same reference numeral is applied to the same constituent element, and redundant description thereof will be omitted.

A first exemplary embodiment will be described below. FIGS. 1A to 1D are a cross-sectional schematic view, a bird's-eye view, a polar coordination, and a plan view illustrating arrangement of transducers of an acoustic probe 100 according to the present exemplary embodiment.

As illustrated in FIG. 1A, the acoustic probe 100 includes a plurality of transducers 104 for receiving acoustic waves and a supporting body 106 having a spherical supporting portion 102 for supporting the transducers 104 to form a spiral array.

Figure 1C:
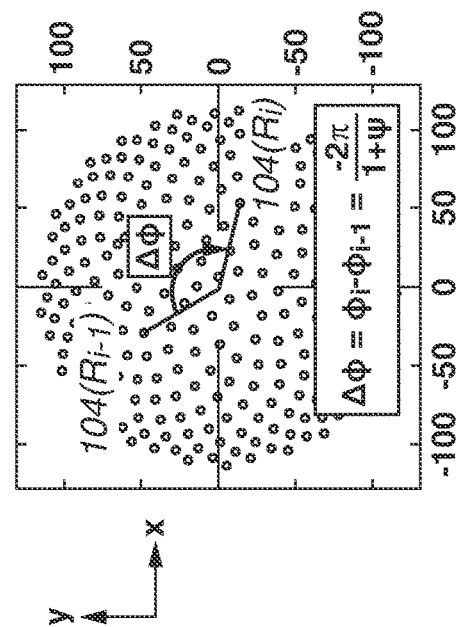
Figure 1D:
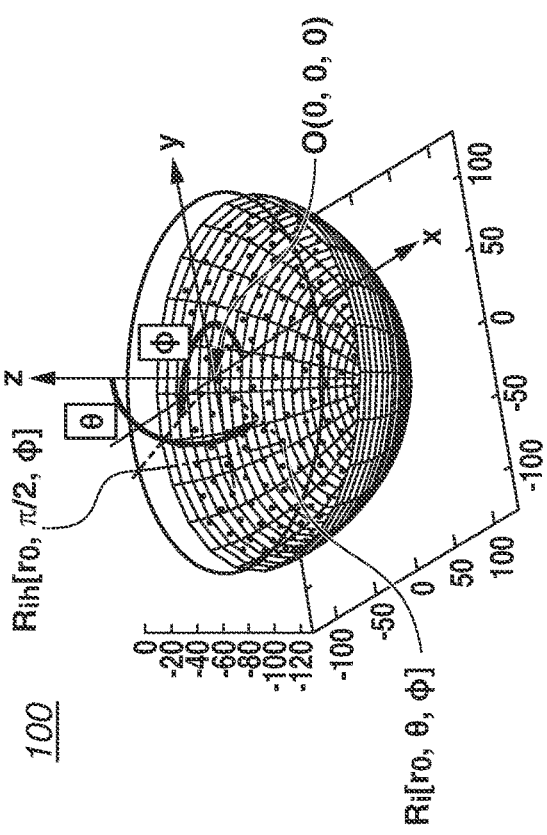

Herein, words and terms used for describing the spiral array in this specification document will be described. As illustrated in FIG. 1C, a position of the transducers 104(Ri) in the spiral array is uniquely expressed as $Ri(r_0, \theta, \varphi)$ [m, rad, rad] by a polar coordinate when a central axis of the spiral array is set as a z-axis, and a curvature center and a curvature radius of the supporting portion 102 are set as "O" and "$r_0$" respectively. In other words, as illustrated in FIG. 1C, a supporting position R of the transducers 104 on the supporting portion 102 is defined as $Ri(r_0, \theta, \varphi)$ [m, rad, rad] by a polar coordinate with respect to the curvature center O of a spherical surface 110 by setting a sphere radius, a zenith angle, and an azimuth angle as "$r_0$", "$\theta$", and "$\varphi$".

Herein, as illustrated in FIG. 1C, the zenith angle $\theta$ conforms to an angle of the transducer 104 with respect to the z-axis viewed from the curvature center O. Similarly, the azimuth angle $\varphi$ conforms to an angle formed by the x-axis and an intersection point Rih between an imaginary plane including the transducers 104 and the z-axis, and the x-y plane. In other words, the azimuth angle $\varphi$ conforms to arctan $(x_i/y_i)$ when a point at which the transducers 104 is orthogonally projected on the x-y plane is set as $Rxy(x_i, y_i)$. The literatures "tan" and "arctan" are used as abbreviations of "tangent" and "arctangent" in this specification.

In the acoustic probe 100 of the present exemplary embodiment, a plurality of transducers 104 is mounted on the supporting portion 102 according to an array rule in which an azimuth angle difference $\Delta\varphi$ between adjacent transducers in the zenith angle $\theta$ is set as a golden angle, while an equal pitch is set with respect to a spiral pitch in the central axis direction.

The acoustic probe which includes the plurality of transducers 104 that satisfy the above-described array rule has high uniformity and high dispersibility in the arrangement of the transducers 104, and thus the artifacts included in the acquired acoustic image can be reduced.

In the present specification, "uniformity" refers to uniformity of an area of a segment on the supporting portion 102 assigned to the plurality of transducers 104, whereas "dispersibility" corresponds to uniformity of a mutual distance between the adjacent transducers from among the plurality of transducers 104.

Further, in the present specification, "$\Psi$ (psi)" is used as a symbol that represents a golden number so that the symbol is distinguished from a lower-case character "$\varphi$ (phi)" that represents an azimuth angle. The golden number $\Psi$ is a positive solution of a quadratic equation $x^2-x-1=0$, and conforms to $(1+\sqrt{5})/2$. Further, an angle [rad] acquired by dividing a circumferential angle $2\pi$ [rad] by 1+golden number $\Psi$ is called as a golden angle, and the golden angle conforms to one angle which is narrower than another angle from among angles acquired by dividing the circumferential angle $2\pi$ [rad] at a golden ratio of $1:\Psi$. The golden angle $2\pi/(1+\Psi)$ is approximated by 137.5 degrees.

In addition, "an azimuth angle difference $\Delta\varphi$ between the adjacent transducers in the zenith angle $\theta$ direction is set as a golden angle" is synonymous with "only one array of transducers 104 spirally arrayed in a Fibonacci array is present", and that is a point different from the reference embodiment described below.

The transducer array according to the present exemplary embodiment can be equivalently described in mutually-different geometric representations.

As the first representation, the plurality of transducers 104 has a certain azimuth angle spiral pitch $\Delta\varphi$ in the azimuth angle $\varphi$ direction and a certain axis direction spiral pitch $\Delta z$ parallel to the central axis direction extending from the center O to an extreme point. The azimuth angle spiral pitch $\Delta\varphi$ is an angle [rad] acquired by dividing a clockwise circumferential angle $-2\pi$ [rad] by 1+golden number $\Psi$, and the pitch is equally set at an equal angle from a starting point to an end point of the spiral array. The azimuth angle spiral pitch $\Delta\varphi$ conforms to an azimuth angle difference $\Delta\varphi(=\varphi_i-\varphi_{i-1})$ between the two closest transducers to each other in the zenith angle $\theta$ direction. Further, the spiral pitch $\Delta z$ in the axis direction conforms to a distance $\Delta z$ ($=r_0 \cos \theta_i - r_0 \cos \theta_{i-1}$) in the z-axis direction between the two closest transducers to each other in the zenith angle $\theta$ direction, and the pitch is set at an equal length from the starting point to the end point of the spiral array.

In the present specification, the supporting portion 102 as a spherical surface portion included in the supporting body 106 has an allowable tolerance in manufacturing compared to a complete sphere. In other words, the allowable tolerance in manufacturing exists in the curvature radius of the supporting portion 102, and a phase difference of the received acoustic wave permits an allowable positional deviation. Specifically, a tolerance of a quarter-wavelength or less is allowed as a tolerance with respect to the spherical surface 110, and a tolerance of ±100 μm of the curvature radius is allowed if a central frequency of 4 MHz is applied as an operating condition of a water-based acoustic matching fluid and the transducers 104.

As the second representation, the plurality of transducers 104 is supported by the supporting portion 102 in a spiral array which satisfies the following general expressions 8, 2, and 3.

$$\Delta\phi = \phi_i - \phi_{i-1} = \frac{-2\pi}{1+\Psi} \qquad (8)$$

$$\Psi = \frac{1+\sqrt{5}}{2} \qquad (2)$$

$$\Delta z = z_i - z_{i-1} = r_0(\cos\theta_i - \cos\theta_{i-1}) = r_0\frac{\cos\theta_{N-1} - \cos\theta_0}{N-1} \qquad (3)$$

Herein, "N" represents a number of transducers mounted on the supporting portion 102, "i" represents an array number (0, 1, ..., N−1) assigned from 0 with respect to each transducer 104 by designating a side having "π" of the zenith angle θ as a starting point.

As the third representation, the plurality of transducers 104 is supported by the supporting portion 102 in a spiral array which satisfies the following general expressions 9, 2, and 5.

$$\phi_i = \frac{-2\pi i}{1+\Psi} \qquad (9)$$

$$\Psi = \frac{1+\sqrt{5}}{2} \qquad (2)$$

$$\theta_i = \cos^{-1}\left[\cos\theta_0 + \frac{\cos\theta_{N-1} - \cos\theta_0}{N-1}i\right] \qquad (5)$$

Herein, "N" represents a number of transducers 104 mounted on the supporting portion 102, "i" represents an array number (0, 1, ..., N−1) assigned from 0 with respect to each transducer 104 by designating a side having "π" of the zenith angle θ as a starting point. Further, the supporting portion 102 shares the curvature center O and the curvature radius $r_0$ with the imaginary-defined spherical surface 110, and includes a portion following the spherical surface 110.

In addition, the azimuth angle φ spiral pitch Δφ of the transducer 104($R_i$) according to the present exemplary embodiment takes a negative value. In other words, because the spiral array of the transducers 104($R_i$) in the azimuth angle direction is arrayed clockwise when viewed from the starting point, a negative sign is applied to a coefficient of an array number "i" of the azimuth angle "$\varphi_i$" in the general expression 9. On the other hand, a variation of the present exemplary embodiment includes a configuration in which the transducers 104($R_i$) are arrayed counterclockwise, and both of the coefficient of the array number "i" of the azimuth angle "$\varphi_i$" in the general expression 9 and the azimuth angle spiral pitch "$\Delta\varphi_i$" in the general expression 6 may take positive values.

The supporting body 106 supports the plurality of transducers 104 and the below-described light irradiation portion 122 to form a certain array to constitute the acoustic probe 100. In an area other than the area of the supporting portion 102, the supporting body 106 assembles a group of cables extending from the plurality of transducers 104, so that the acoustic probe 100 can be operated and moved favorably. Generally, although the operability of the acoustic probe 100 will be lowered when the number of channels for receiving the acoustic wave signals is increased, the supporting body 106 addresses this problem. The function of organizing the cable group is more effective when the acoustic probe 100 is applied to a handheld probe (not illustrated).

Further, a piezo-type transducer having a pyroelectric ceramic, a capacitance-type transducer having a cavity between electrodes, or a transducer provided with the Fabry-Perot interferometer may be employed as the transducer 104. A piezo ceramic material as represented by lead zirconate titanate (PZT) or a polymeric piezoelectric membrane material as represented by polyvinylidene fluoride (PVDF) may be used as a constituent member of the piezo-type transducer 104. Furthermore, a transducer of any type may be used as long as an electric signal can be output by receiving an acoustic wave.

Further, the electric signal acquired by the transducer 104 is a time-resolved signal. In other words, an amplitude of the electric signal acquired by a reception element represents a value based on acoustic pressure received ty the transducer at each time, e.g., a value proportional to the acoustic pressure. Typically, a frequency bandwidth of the acoustic wave coming from a living subject is 100 kHz or more and 100 MHz or less. Therefore, it is desirable for the transducer 104 to have receiving sensitivity in the frequency bandwidth of at least 100 kHz or more and 100 MHz or less.

The spiral array of the transducers 104 of the acoustic probe 100 according to the present exemplary embodiment has a zenith angle $\theta_0$ of 177.0632-degree at the starting point and a zenith angle $\theta_{255}$ of 109.2017-degree at the ending point.

Reference Embodiment

FIG. 2A is an x-y plan view illustrating a transducer array of an acoustic probe 900 according to a reference embodiment, and FIGS. 2B and 2C are plan views respectively illustrating transducer arrays 901 and 902 constituting the acoustic probe 900.

In the acoustic probe 900 of the reference embodiment, a spiral array 901 of 128 elements of transducers 904 and a spiral array 902 of 128 elements of transducers 914, each arrayed at a spiral pitch in an azimuth angle direction, which are both twice as large as the golden angle, are superimposed. In other words, the acoustic probe 900 of the reference embodiment includes two spiral arrays, each arrayed at the spiral pitch in the azimuth angle direction, which do not form the golden angle.

The spiral array 901 in FIG. 2B corresponds to positions of 128 elements of the transducers 904 ($S_0$, $S_1$, ..., $S_i$, ..., $S_{127}$) respectively, and follows a spiral rule that satisfies the general expressions 10, 2, 11, and 12.

$$\Delta\phi_{2a} = \phi_i - \phi_{i-1} = \frac{-2\pi}{1+\Psi} \times 2 \qquad (10)$$

$$\Psi = \frac{1+\sqrt{5}}{2} \qquad (2)$$

$$\delta = 0 \qquad (11)$$

$$\phi_{2a} = \frac{-2\pi}{1+\Psi} \times 2i + \delta = \frac{-4\pi}{1+\Psi}i \qquad (12)$$

FIG. 2B illustrates an azimuth angle difference $\Delta\varphi_i$ between two points 904($S_{i-1}$) and 904 ($S_i$) which are closest to each other in the zenith angle direction θ, and a starting point 904($S_0$) of the spiral array 901. It can be seen that the azimuth angle difference $\Delta\varphi_i$ between the two closest points 904 ($S_{i-1}$) and 904($S_i$) to each other in the zenith angle direction is an angle $-4\pi/\Psi$ [rad], which corresponds to an angle twice as large as the clockwise golden angle.

Further, the spiral array 902 in FIG. 2C corresponds to positions of 128 elements of transducers 914 ($T_0$, $T_1$, ..., $T_i$, ..., $T_{127}$) respectively, and follows a spiral rule that satisfies the general expressions 13, 2, 14, and 15.

$$\Delta\phi_{2b} = \phi_i - \phi_{i-1} = \frac{-2\pi}{1+\Psi} \times 2 \qquad (13)$$

$$\Psi = \frac{1+\sqrt{5}}{2} \qquad (2)$$

$$\delta = \frac{-2\pi}{1+\Psi} \qquad (14)$$

$$\Delta\phi_{2b} = \frac{-2\pi}{1+\Psi} \times 2i + \delta = \frac{-4\pi}{1+\Psi}\left(i + \frac{1}{2}\right) \qquad (15)$$

The spiral array 902 conforms to a spiral array acquired by rotating the spiral array 901 by an angle $-2\pi/(1+\Psi)$ [rad] that is one-half angle of the azimuth angle spiral pitch common to the two spiral arrays 901 and 902.

FIG. 2C illustrates the two closest points 914 ($T_{i-1}$) and 914($T_i$) to each other in the zenith angle θ direction, and a starting point 914($T_0$) of the spiral array 902.

Because each of the two spiral arrays 901 and 902 has one transducer 904($S_i$) or 914($T_i$) at the same zenith angle θ, the spiral arrays 901 and 902 do not interfere with each other on the supporting portion 102 if azimuth angles δ [rad] of spiral starting points i (i=0) do not coincide with each other.

On the condition that the azimuth angle δ at the spiral starting point of the spiral array 902 corresponds to an angle $-2\pi/(1+\Psi)$ [rad] that is one-half angle of the common azimuth angle spiral pitch, the elements of the spiral arrays 901 and 902 having the same zenith angle θ do not come close to each other. The acoustic probe 900 of this reference embodiment appears to have spiral arrays of transducers 904 and 914 with uniform dispersibility secured.

Figure 3A:
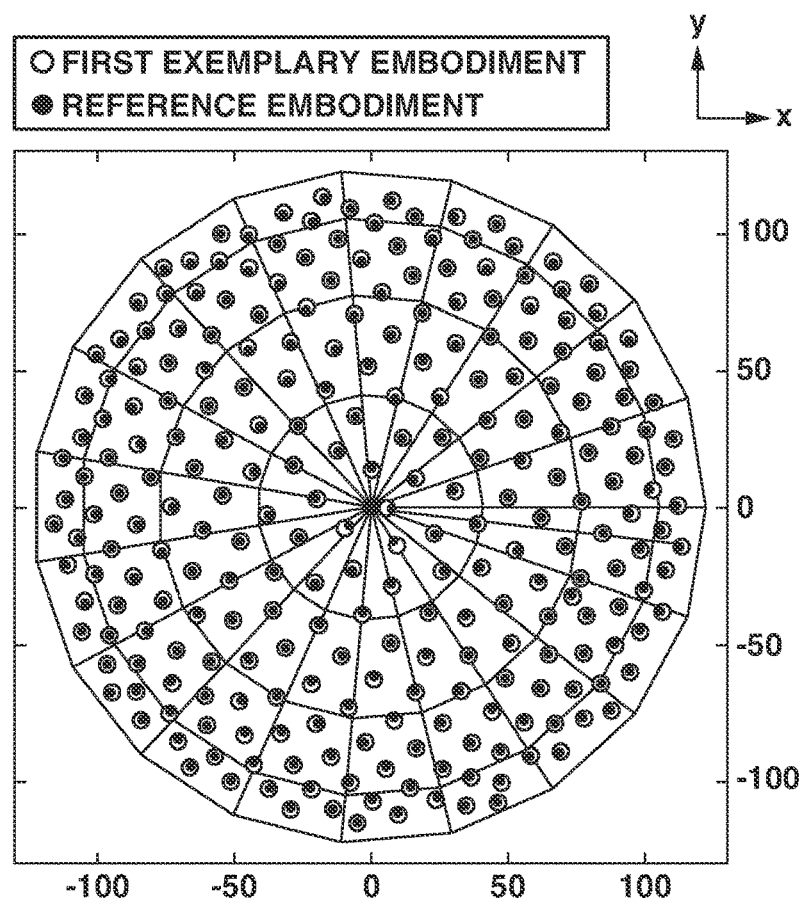
FIG. 3A is a plan view illustrating acoustic probes of the first exemplary embodiment and the reference embodiment overlapping with each other on an x-y plane.
Figure 3B:
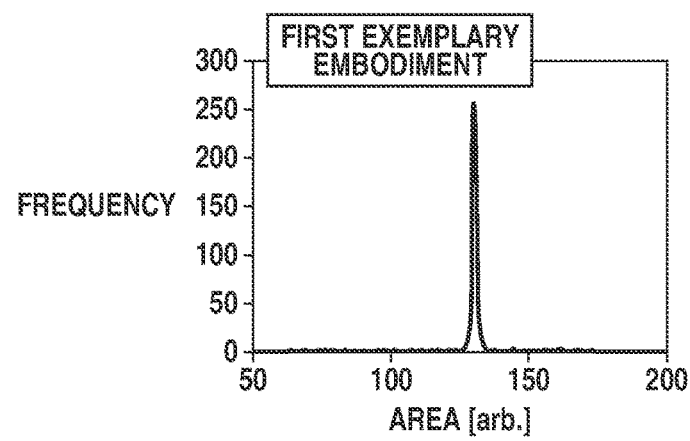
FIGS. 3B and 3C are frequency distribution graphs of effective reception areas of the respective acoustic probes of the first exemplary embodiment and the reference embodiment.
Figure 3C:
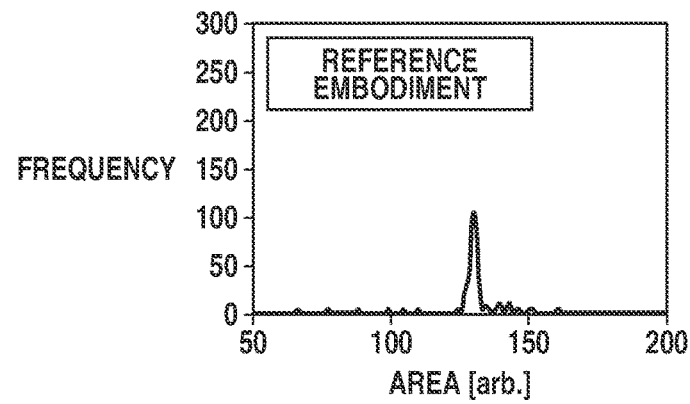

FIG. 3A is a plan view illustrating acoustic probes of the first exemplary embodiment and the reference embodiment, which are superimposed on an x-y plane. FIGS. 3B and 3C are frequency distribution graphs of effective cover areas of the acoustic probes of the first exemplary embodiment and the reference embodiment, respectively.

As illustrated in FIG. 3A, white dots representing the positions of the transducers 104 according to the first exemplary embodiment and black dots representing the positions of the transducers 904 or 914 according to the reference embodiment are largely apart in a vicinity of the extreme point where the z-axis passes through.

On the other hand, FIG. 3B is a frequency distribution graph illustrating frequency of the effective cover area of one element of the transducers 104 of the acoustic probe 100 according to the first exemplary embodiment. Similarly, FIG. 3C is a frequency distribution graph illustrating frequency of an effective cover area of one element of the transducers 904 or 914 of the acoustic probe 900 according to the reference embodiment. The frequency of the effective cover area is calculated through a method using the Voronoi diagram.

From the graphs in FIGS. 3B and 3C, it can be seen that the acoustic probe 100 according to the first exemplary embodiment has uniform dispersibility of transducers at least two times higher than that of the acoustic probe 900 according to the reference embodiment. This difference in the uniform dispersibility of transducers seen in FIGS. 3B and 3C confirms that the two acoustic probes 100 and 900 observed in a vicinity of the extreme point illustrated in FIG. 3A do not coincide with each other.

In other words, the acoustic probe 100 according to the first exemplary embodiment which includes one spiral array arrayed at the spiral pitch which is a golden angle in the azimuth angle φ direction has uniform dispersibility of transducers higher than that of the acoustic probe 900 according to the reference embodiment in which the spiral pitch in the azimuth angle φ direction is not a golden angle. Accordingly, an effect of reducing the artifact is higher in the acoustic probe 100 according to the first exemplary embodiment having one spiral array arrayed at the spiral pitch of a golden angle in the azimuth angle φ direction than in the acoustic probe 900 of the reference embodiment in which the spiral pitch in the azimuth angle φ direction is not a golden angle.

Figure 4A:
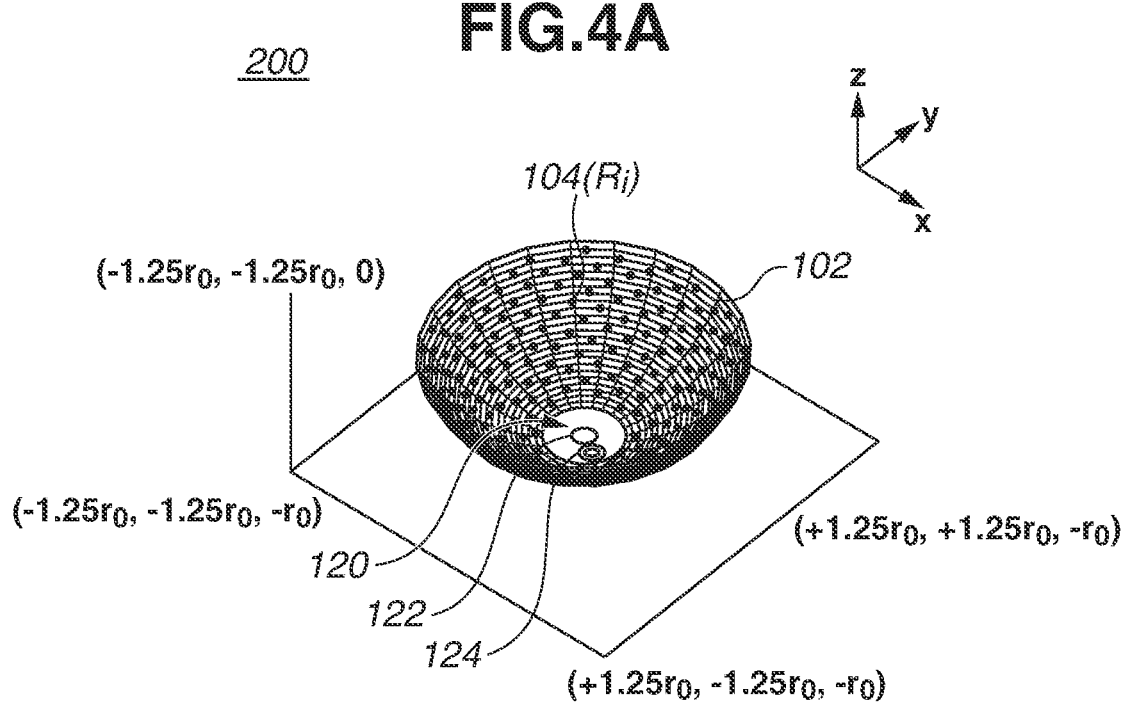
FIG. 4A is a bird's-eye view of an acoustic probe according to a second exemplary embodiment.
Figure 4B:
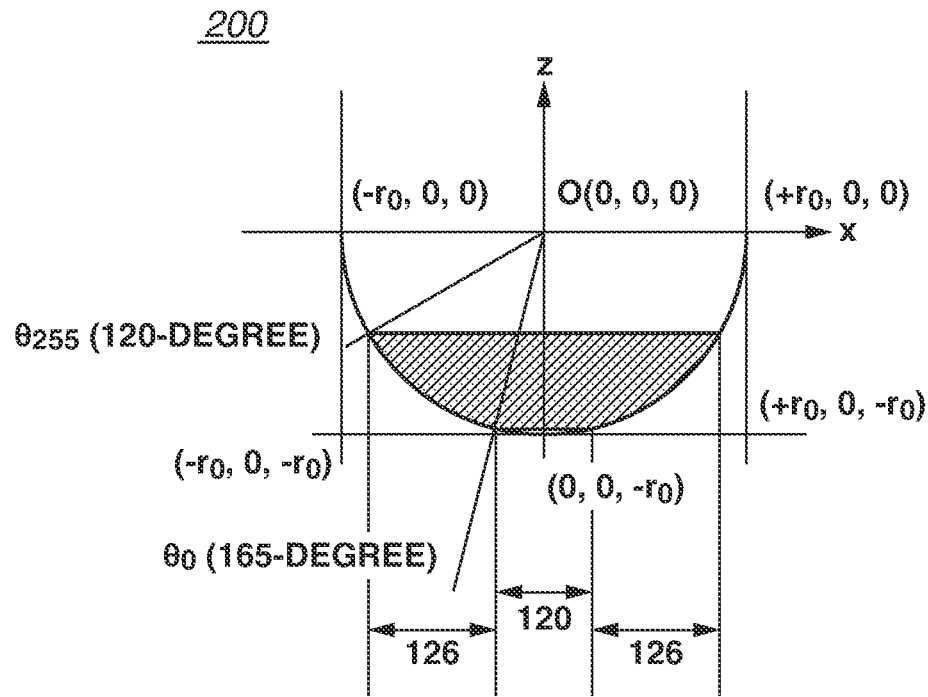
FIG. 4B is a schematic projection view illustrating the acoustic probe projected on an x-y plane.

Hereinafter, a second exemplary embodiment will be described. FIG. 4A is a bird's-eye view of an acoustic probe 200 according to the present exemplary embodiment, and FIG. 4B is a schematic projection view illustrating the acoustic probe 200 projected on an x-y plane. The acoustic probe 200 of the present exemplary embodiment is different from the acoustic probe 100 of the first exemplary embodiment in that a non-arrangement portion 120 where the transducers are not arranged is provided in a vicinity of an extreme point (0, 0, $r_0$) of the supporting portion 102.

The acoustic probe 200 of the present exemplary embodiment will be described below in detail. In principle, the same reference numeral is applied to the same constituent element as the first exemplary embodiment, and description thereof will be omitted.

As illustrated in FIGS. 4A and 4B, the acoustic probe 200 of the present exemplary embodiment includes 256 elements of transducers 104 arrayed in a Fibonacci array. The spiral array of the transducers 104 of the present exemplary embodiment has a zenith angle $\theta_0$ of 165-degree (11/12 rad) at the starting point and a zenith angle $\theta_{255}$ of 120-degree (π rad) at the ending point. In other words, the non-arrangement portion 120 is a part of the supporting portion 102 having the zenith angle θ greater than 165-degree and 180-degree or less, and the arrangement portion 126 is a part of the supporting portion 102 having the zenith angle θ of 120-degree or more and 165-degree or less.

A light irradiation portion 122 is arranged at a position overlapping with the extreme point (0, 0, $r_0$) of the supporting portion 102 in the acoustic probe 200 so that light is emitted toward the curvature center O of the supporting portion 102. Because light is emitted toward the curvature center O of the supporting portion 102, the acoustic probe 200 can symmetrically irradiate a region of interest with light. Therefore, it is possible to reduce lowering of a photoacoustic signal in a periphery of the region of interest. As long as the light irradiation portion 122 is arranged such that light is emitted to a test subject 801, the irradiation direction does not have to be set toward the curvature center O. However, from the viewpoint of reducing the lowering of the photoacoustic signal in the periphery of the region of interest, it is preferable that the irradiation direction be set toward the curvature center O. In other words, the light irradiation portion 122 arranged on the acoustic probe 200 is supported by the supporting portion 102 at a position having a zenith angle greater than the zenith angle $\theta_0$ at the starting point of the spiral array of the transducers 104. It is preferable that the light irradiation portion 122 and the transducers 104 be arranged at positions where the light irradiation portion 122 and the transducers 104 do not interfere with each other so that irradiation of light and reception of acoustic waves can be prevented from being interrupted by one another.

The light irradiation portion 122 can be configured using an optical element such as a lens, a mirror, or an optical fiber. When the breast is the test subject 801, it is preferable that irradiation light be emitted by widening a beam diameter. Therefore, the light irradiation portion 122 may be configured of a diffuser panel that diffuses light. On the other hand, in a photoacoustic microscope, to increase the resolution, a light output portion of the light irradiation portion 122 may be configured of a lens, with which a beam of light may be focused and emitted.

Further, a port 124 for supplying or discharging an acoustic matching liquid is arranged at the non-arrangement portion 120 inside the supporting portion 102, i.e., on a side of the curvature center O of the supporting portion 102, together with the light irradiation portion 122. According to the acoustic probe 200 of the present exemplary embodiment, an acoustic matching liquid (not illustrated), which is managed to have a certain quality and a certain acoustic propagation characteristic, can be supplied in a right amount at necessary timing and discharged with a little residual. In other words, the acoustic probe 200 includes the port 124 for supplying or discharging the acoustic matching liquid in a position having a zenith angle greater than the zenith angle $\theta_0$ at the starting point of the spiral array of the transducers 104.

Further, a camera (not illustrated) having an imaging field facing toward the test subject 801 or an illumination lamp (not illustrated) for securing the imaging illuminance of the camera can be arranged at the non-arrangement portion 120. In other words, the acoustic probe 200 of the above-described exemplary embodiment includes a camera having an imaging field facing toward the test subject 801 or the illumination lamp at a position having a zenith angle greater than the zenith angle $\theta_0$ at the starting point of the spiral array of the transducers 104.

Similar to the acoustic probe 100 of the first exemplary embodiment, 256 elements of the transducers 104 included in the acoustic probe 200 are arrayed at the arrangement portion 126 in a Fibonacci array with high uniform dispersibility. Accordingly, similar to the case of the acoustic probe 100 of the first exemplary embodiment, an effect of reducing the artifacts included in the acquired reconstructed image can be produced even though the acoustic probe 200 includes the non-arrangement portion 120.

Although the zenith angle $\theta_0$ at the starting point of the acoustic probe 200 of the present exemplary embodiment is 165 degrees (=$11\pi/12$ rad), the exemplary embodiment of the present invention is not limited thereto. Of the plurality of transducers 104, the starting point of the spiral array having the greatest zenith angle $\theta$ can take the zenith angle $\theta_0$ of $8\pi/9$ [rad] or more and $\pi$ [rad] or less.

Similarly, although the zenith angle $\theta_{255}$ at the ending point of the acoustic probe 200 of the present exemplary embodiment is 120 degrees (=$2\pi/3$ rad), the exemplary embodiment of the present invention is not limited thereto. In the spiral array having N-elements of transducers 104, the ending point of the spiral array having the smallest zenith angle $\theta$ among the plurality of transducers 104 can take a zenith angle $\theta_{N-1}$ of $\pi/3$ [rad] or more and $3\pi/4$ [rad] or less.

Figure 5A:
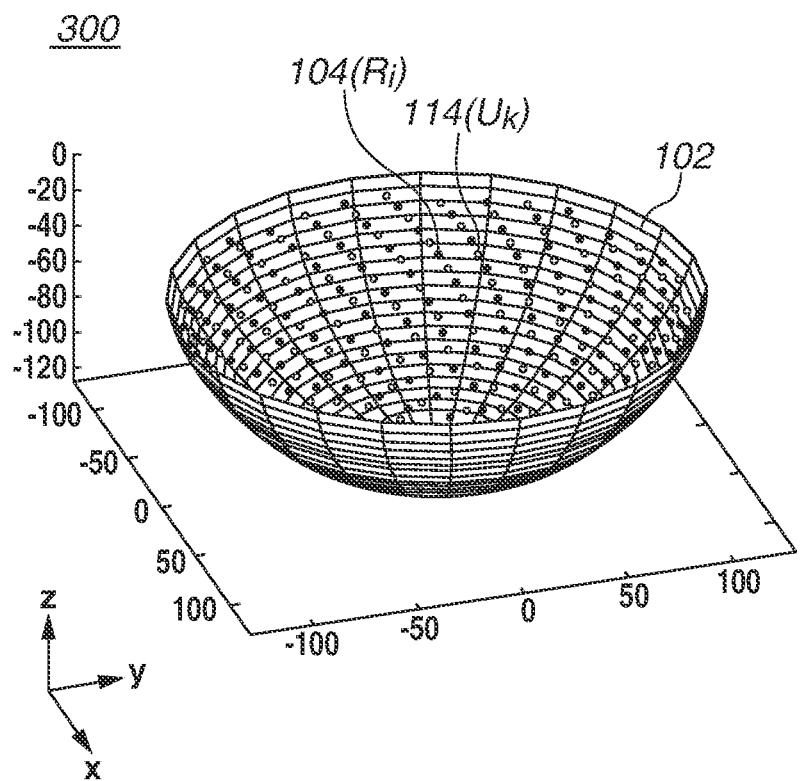
FIGS. 5A and 5B are bird's-eye views illustrating an acoustic probe according to a third exemplary embodiment.
Figure 5B:
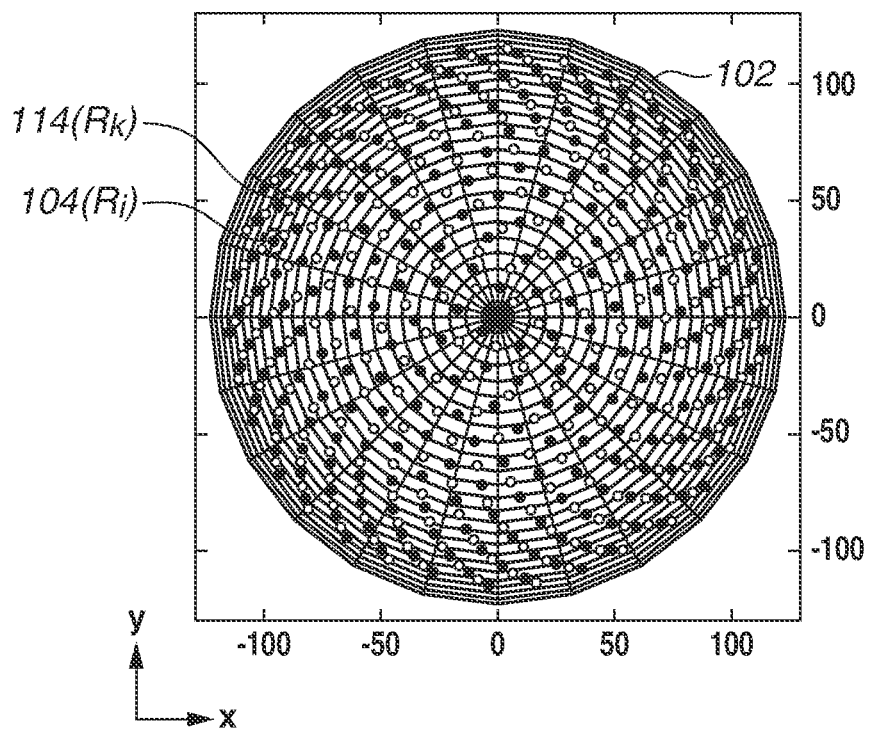

A third exemplary embodiment will be described below. FIGS. 5A and 5B are bird's-eye views illustrating an acoustic probe 300 according to the present exemplary embodiment. The acoustic probe 300 of the present exemplary embodiment is different from the acoustic probe 100 of the first exemplary embodiment in that the acoustic probe 300 includes a plurality of light irradiation portions 114 arrayed in a spiral state. The acoustic probe 300 of the present exemplary embodiment can improve a signal-to-noise (S/N) ratio of an acquired acoustic signal in addition to producing an artifact reduction effect caused by high uniform dispersibility of the transducers 104. The acoustic probe 300 of the present exemplary embodiment will be described below in detail.

In principle, the same reference numeral is applied to the same constituent element as the first or the second exemplary embodiment, and description thereof will be omitted.

The acoustic probe 300 of the present exemplary embodiment includes a plurality of transducers 104 ($R_0, R_1, \ldots, R_i, \ldots$) and a plurality of light irradiation portions 114 ($U_0, U_1, \ldots, U_k, \ldots$) spirally arrayed on the supporting portion 102 according to an array rule in common with the array rule described in the first exemplary embodiment.

The plurality of light irradiation portions 114($U_k$) of the present exemplary embodiment is spirally arrayed on the supporting portion 102 to satisfy general expressions 16, 2, and 7.

$$\phi_j = \frac{-2\pi j}{1+\Psi} + \xi \tag{16}$$

$$\Psi = \frac{1+\sqrt{5}}{2} \tag{2}$$

$$\theta_j = \cos^{-1}\left[\cos\theta_0 + \frac{\cos\theta_{M-1} - \cos\theta_0}{M-1}j\right] \tag{7}$$

Herein, "M" represents a number of light irradiation portions 114 included in the acoustic probe 300, "j" represents an array number (0, 1, ..., M−1) assigned from 0 to each transducer 104 by designating a "$\pi$" side of the zenith angle $\theta$ as a starting point, and "$\xi$ (xi)" represents an azimuth angle difference between the starting point $U_0$ of the array of the light irradiation portions 114 and the starting point $R_0$ of the array of the transducers 104.

The azimuth angle spiral pitch $\Delta\varphi$ of the light irradiation portions 114($U_k$) according to the present exemplary embodiment takes a negative value. In other words, because the spiral array of the light irradiation portions 114($U_k$) in the azimuth angle direction is arrayed clockwise when viewed from the starting point, a negative sign is applied to a coefficient of an array number "j" of the azimuth angle "$\varphi_j$" in the general expression 16. On the other hand, as a variation of the present exemplary embodiment, the transducers 104($R_j$) and the light irradiation portions 114($U_k$) can be arrayed counterclockwise if a common azimuth angle spiral pitch is applied thereto. Therefore, both of the coefficient of the array number "j" of the azimuth angle "$\varphi_j$" and the azimuth angle spiral pitch $\Delta\varphi_j$ in the general expression 16 may take positive values.

The general expression 16 is different from the general expression 9 in that an angle $\xi$ [rad] having a value other than zero is added to the azimuth angle $\varphi_0$. In other words, the spiral array of the light irradiation portions 114 has an azimuth angle spiral pitch of $-2\pi/(1+\Psi)$ (=$\Delta\varphi$) and an axis direction spiral pitch $\Delta z$ which are in common with the spiral array of the transducers 104, and has a starting point different from the starting point of the spiral array of the transducers 104.

Because the transducer 104($R_i$) of the acoustic probe 300 is located according to the azimuth angle $\varphi_i$ and the zenith angle $\theta_i$ of the general expression 2, another transducer is not arranged at the zenith angle at which the optional transducer $104(R_i)$ is arrayed. In other words, the light irradiation portions $114(U_k)$ can be spirally arrayed on the supporting portion 102 without interfering with the transducers $104(R_i)$ because spiral pitch conditions are common to the transducers 104 except for the condition of the azimuth angle of the starting point.

Because the light irradiation portions $114(U_k)$ of the present exemplary embodiment are arranged with uniform dispersibility similar to the transducers 104, the acoustic probe 300 can uniformly irradiate the test subject 801 with light in an optional direction in which the acoustic probe 300 faces the test subject 801.

Further, although it is preferable that "π" [rad] be used as the azimuth angle δ corresponding to the light irradiation portion $114(U_0)$ at the starting position, another azimuth angle may be used as long as the transducers 104 and the light irradiation portions 114 do not physically interfere with each other. Further, in the present exemplary embodiment, the numbers M and N of the elements mounted on the supporting portion 102 satisfy a condition "M=N=256". However, the element number M of the light irradiation portions 114 and the element number N of the transducers 104 do not need to coincide with each other if the conditions are set with respect to the spiral pitches Δφ and Δz, and the condition is met that the azimuth angles of respective starting points are different from one another.

According to the acoustic probe 300 of the present exemplary embodiment, light can be emitted to a wider range because the plurality of light irradiation portions $114(U_k)$ is arranged with uniform dispersibility. Accordingly, it is possible that a greater amount of light reaches the region-of-interest ROI located inside the test subject 801 while the maximum permissible exposure (MPE) is kept as the maximum permissible illuminance. With this configuration, acoustic pressure of the photoacoustic wave generated in the region-of-interest ROI is increased, so that the S/N ratio of the photoacoustic signal can be improved. Further, if the present exemplary embodiment is applied to an acoustic apparatus capable of acquiring volume data of a test subject, an effect of reducing the artifacts generated in the volume data can be also produced, and thus an acoustic image (reconstructed image) with higher precision can be acquired.

If the curvature radius $r_0$ of the supporting portion 102 is read as 127 mm, the scales of the orthogonal coordinate axes in FIGS. 4A and 4B coincide with the scales of the orthogonal coordinate axes in FIGS. 1B to 1D, FIGS. 2A, 2B, 3A, 5A, and 5B.

Figure 6:
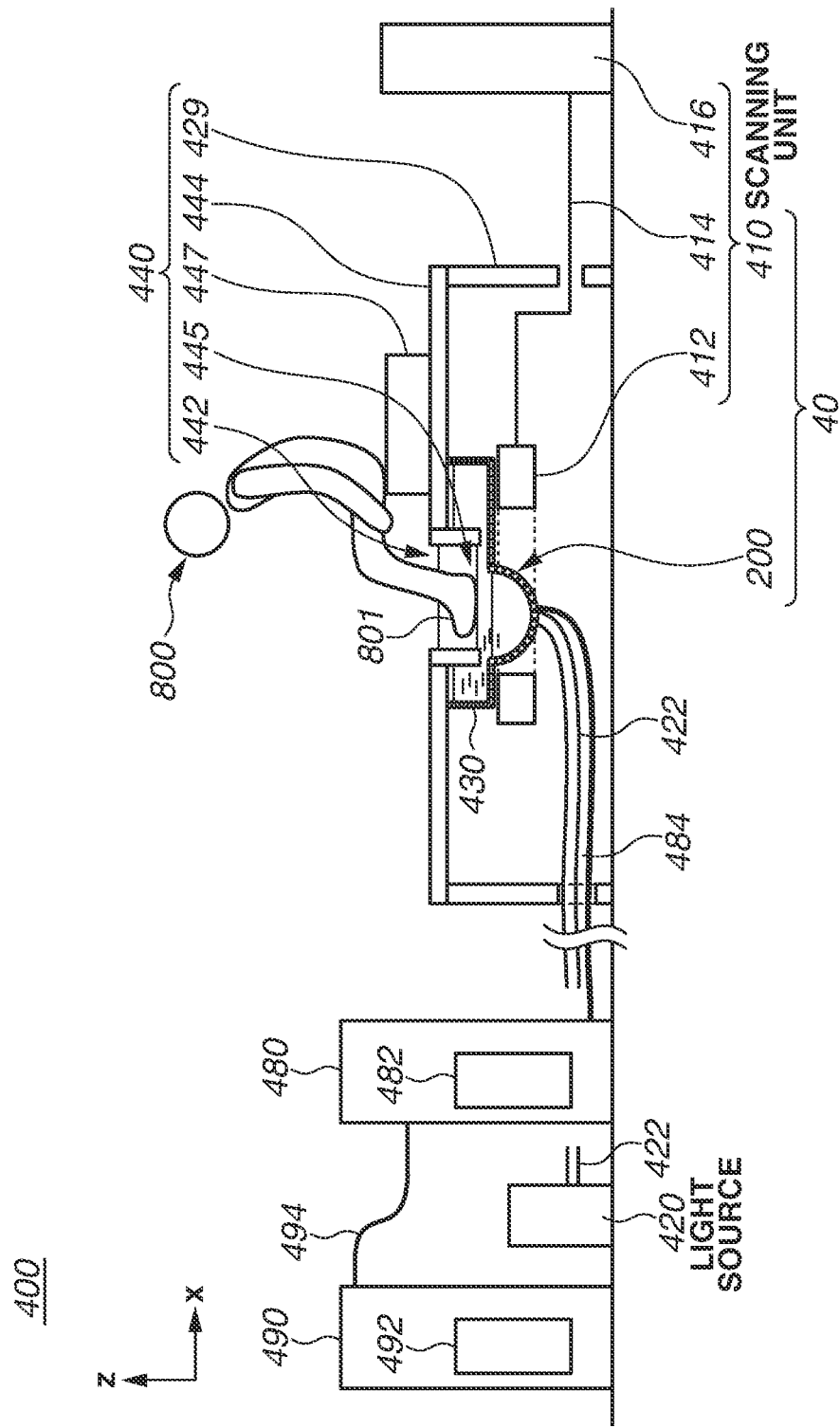
FIG. 6 is a schematic diagram illustrating an acoustic apparatus according to a fourth exemplary embodiment.

A fourth exemplary embodiment will be described below. FIG. 6 is a schematic diagram illustrating an acoustic apparatus 400 according to the present exemplary embodiment.

The acoustic apparatus 400 of the present exemplary embodiment includes a holding unit 440, the acoustic probe 200 according to the second exemplary embodiment, a liquid tank 430 including the acoustic probe 200, and a scanning unit 410 that moves the liquid tank 430 in parallel in a substantially horizontal plane. In other words, a scanning unit 410 that moves the liquid tank 430 in translation motion in a substantially horizontal plane. Respective elements will be described below.

As illustrated in FIG. 6, the holding unit 440 includes an insertion opening 442 through which a test subject 801 is inserted as a part of an examinee 800, and a holding stand 444 for holding the examinee 800. As illustrated in FIG. 6, the holding unit 440 further includes a holding portion 445 for holding the inserted test subject 801, a seat 447 for the examinee 800 to take, and a side face panel 429 continuously connected with circumferential four sides of the holding stand 444.

The seat 447 is disposed on the holding stand 444 in order to stabilize a posture of the examinee 800 at the time of imaging. Further, the side face panel 429 is disposed to surround the liquid tank 430 that is moved when an image is captured, an XY stage 412, and a light irradiation portion (not illustrated) included in the acoustic probe 200, to separate an inner portion of the acoustic apparatus 400 from a moving space of the examinee 800 or an operator (not illustrated). In order to reduce a burden of the examinee 800 at the time of imaging, a cushion (not illustrated) may be placed on the holding stand 444 or the seat 447.

The insertion opening 442 is an opening provided on the holding stand 444 so that the test subject 801 as a part of the examinee 800 can be inserted thereto. A part of the examinee 800 which is not inserted to the insertion opening 442 can be placed on the holding stand 444, so that the imaging posture of the examinee 800 can be stabilized. Although an imaging target part may be the upper limb, the lower limb, the head area, or the breast of the examinee 800, an imaging posture in FIG. 6 illustrates a seated state where the left foot regarded as the test subject 801 is inserted to the insertion opening 442 while the right foot (not illustrated) is placed on a placement portion of the holding stand 444.

The holding portion 445 is fixed to the holding stand 444 at a position overlapping with the insertion opening 442 so that the test subject 801 can be stabilized when imaging is executed. The holding portion 445 is formed into a semi-container shape projected downward from the holding stand 444, so that the test subject 801 can be held on the lower side of the holding stand 444.

The holding portion 445 further includes an acoustic matching member having an acoustic propagation characteristic which enables the acoustic probe 200 to receive an acoustic wave propagated from the test subject 801. A resin material such as isoprene rubber (IR), silicon rubber, or polyethylene terephthalate which transmits infrared light is used for the acoustic matching member. The exemplary embodiment of the present invention also includes a configuration in which a mesh-type resin material having the rigidity higher than the resin material is attached to the holding portion 445 so that the lower end of the holding position can be reinforced in a case where the above-described resin material has flexibility.

It is preferable that the holding portion 445 have a sealing characteristic to divide a space so that the test subject 801 can be prevented from coming into direct contact with the acoustic matching liquid retained in the liquid tank 430. With this configuration, hygienic condition of the acoustic matching liquid retained in the liquid tank 430 can be secured. The above-described holding portion 445 having the sealing characteristic and the semi-container shaped projection portion can sonically connect the test subject 801 with the holding portion 445 while retaining the acoustic matching liquid.

In addition, to relieve the examinee 800 from a sense of insecurity, a handrail or a protective fence (not illustrated) may be disposed on the holding unit 440 as appropriate.

A receiving/scanning unit 40 is located on the lower side of the holding stand 444, and includes the acoustic probe 200 for receiving the acoustic wave propagated from the test subject 801 inserted through the insertion opening 442 and a scanning unit 410 that two-dimensionally moves the acoustic probe 200 parallel to the horizontal plane.

The XY stage 412 is configured to move the acoustic probe 200 substantially parallel to the horizontal plane and two-dimensionally relative to the insertion opening 442. Based on a scan signal output from the below-described scanning control unit 416, the XY stage 412 enables the acoustic probe 200 to execute scanning in an optional two-dimensional scanning pattern such as rotational scanning, spiral scanning, boustrophedon scanning, or raster scanning. In other words, the liquid tank 430 is connected to the scanning unit 410 which executes scanning by changing a position of the acoustic probe 200 relative to the test subject 801.

The scanning unit 410 includes the scanning control unit 416 for outputting a scan signal to the XY stage 412 and a scan signal cable 414 for connecting the XY stage 412 and the scanning control unit 416.

The scanning control unit 416 is disposed outside the holding unit 440, and outputs the scan signal to the XY stage 412 via the scan signal cable 414. The scan signal cable 414 is wired via a cable opening provided on the side face panel 429. Alternatively, the scan signal cable 414 can be omitted if the scan signal is transmitted wirelessly.

"Horizontality" in the present specification refers to a physical quantity measurable by a level or a laser displacement meter. Inclination of the horizontality has an effective allowance in the acoustic apparatus 400 according to the present exemplary embodiment, and an upper limit or a lower limit of "tan θ" which corresponds to an inclination angle falls within a range of ±0.5 mm/m relative to complete horizontality vertical to a perpendicular direction. The upper limit and the lower limit of "tan θ" corresponding to the inclination angle may preferably be limited to a range of ±0.1 mm/m, or more preferably, a range of ±0.04 mm/m.

The acoustic apparatus 400 of the present exemplary embodiment is provided with the acoustic probe 200 and the liquid tank 430 that is two-dimensionally scanned together with the acoustic matching liquid. Thus, the retained acoustic matching liquid may flow, generate waves, or hold air bubbles in the course of scanning operation.

It is particularly preferable to apply the acoustic probe 200 including the transducers 104 spirally arrayed with high uniform dispersibility to the above-described acoustic apparatus 400 including the liquid tank 430 connected to the XY stage 412.

The acoustic apparatus 400 of the present exemplary embodiment further includes a plurality of signal lines 484 for transmitting the acoustic wave signals output respectively from the transducers 104 and a signal relaying device 480 electrically connected to the acoustic probe 200 via the plurality of signal lines 484.

The acoustic probe 200 of the present exemplary embodiment outputs the received acoustic wave as an analog acoustic wave signal. Accordingly, the signal lines 484 have a number of channels corresponding to the number of elements of the transducers 104 ($R_0$, $R_1$, . . . , $R_i$, . . . ) included in the acoustic probe 200 to serve as parallel transmission cables that transmit the analog acoustic signals of respective channels in parallel. The parallel transmission cables is a group of cables in which all or a part of the signal lines 484 are bundled.

The signal relaying device 480 includes an analog-digital (AD) converter 482 for converting the analog acoustic signals transmitted in parallel from the acoustic probe 200 into digital acoustic signals.

The acoustic apparatus 400 further includes an integrated control unit 490 connected to the signal relaying device 480 via a serial cable 494. The integrated control unit 490 includes a signal processing unit 492 which receives the digital acoustic signals output from the signal relaying device 480 and acquires volume data of the test subject 801 by executing image reconstruction processing. The serial cable 494 transmits the digital signals in a temporal sequence. In other words, the acoustic apparatus 400 includes the signal processing unit 492 which acquires information about the test subject 801 based on a signal received by the acoustic probe 200.

The signal processing unit 492 included in the integrated control unit 490 executes reconstruction processing of digital acoustic wave signals output from the signal relaying device 480, and outputs a captured image to a storage medium or a display unit (not illustrated). The integrated control unit 490 can output a control instruction to the scanning control unit 416, a liquid supply mechanism (not illustrated), and a temperature control mechanism (not illustrated).

Further, as illustrated in FIG. 6, the acoustic probe 200 of the present exemplary embodiment includes a light irradiation portion (not illustrated) optically connected to a light source 420 which outputs near-infrared pulse light. The light irradiation portion is optically connected to the light source 420 via an optical fiber 422 capable of transmitting near-infrared light. The acoustic probe 200 is configured to receive the photoacoustic wave which is generated inside the test subject 801 because of the near-infrared light emitted from the light irradiation portion. In addition, although the light irradiation portion 122 illustrated in FIG. 4A is omitted from the acoustic apparatus 400 in FIG. 6, the light irradiation portion 122 is scanned by the scanning unit 410 together with the plurality of transducers 104 (acoustic probe 200).

<Light Source 420>

A pulse width of light emitted from the light irradiation portion 122 may be a pulse width of 1 ns or more and 100 ns or less. Further, a wavelength of light emitted from the light irradiation portion 122 may be a wavelength falling within a range of 400 nm or more and 1600 nm or less. When an image of a blood vessel in a vicinity of a surface of a living subject is captured, it is possible to use light of a wavelength of 400 nm or more and 700 nm or less which is considerably attenuated in the blood vessel. On the other hand, when an image of a deep portion of the living subject is captured, it is possible to use light of a wavelength of 700 nm or more and 1000 nm or less, which is less likely to be absorbed by a background tissue such as fluid or fat of the living subject.

A laser or a light-emitting diode may be used as the light source 420. Further, in a configuration in which photoacoustic waves are received by switching light between a plurality of wavelengths, a light source capable of converting the wave length of irradiation light may be used. In a case where irradiation of the test subject 801 is performed by switching between the plurality of wave lengths, a plurality of light sources for generating light of different wave lengths may be prepared, so that light can be alternately emitted from the respective light sources. In the present specification, a term "light source" is used to mean a single light source as well as a plurality of light sources.

Various lasers such as a solid-state laser, a gas laser, a dye laser, and a semiconductor laser may be used for the laser optically connected to the light irradiation portion 122. For example, a pulse laser such as a neodymium-doped yttrium aluminum garnet (Nd:YAG) laser or an alexandrite laser may be used as the light source 420.

Further, a titanium-sapphire (Ti:sa) laser or an optical parametric oscillator (OPO) laser that Nd:YAG laser light excites serving as excitation light may be used as the light source 420. Furthermore, a microwave source may be used as the light source 420.

In addition, the test subject 801 becomes a target of photoacoustic measurement if the test subject 801 contains a light absorbing body having a photoacoustic characteristic. The above-described light absorbing body may be a blood component such as hemoglobin, glycogen, or cholesterol, or may be melanin or a hair root. Further, the light absorbing body may be a pigment such as methylene blue (MB) or indocyanine green (ICG), a gold fine particle, or may be a material integrating or chemically modifying the pigments or gold fine particles introduced from the outside.

Accordingly, if the acoustic apparatus 400 according to the present exemplary embodiment is used as a photoacoustic apparatus, a concentration distribution of the light-absorbing bodies locally existing in the background tissue such as fat is acquired as volume data. With respect to a disease such as a malignancy or a blood vessel disease in which a significant correlation with a signal intensity of the light-absorbing body is observable, the acoustic apparatus 400 is used for supporting diagnostic reading of tumor malignancy or used for observing progress of chemotherapy. Application of photoacoustic measurement is expected with respect to a disease such as a malignancy accompanied by new blood vessels or plaque accumulated on the carotid wall.

In the present specification, the acoustic probe used for the photoacoustic imaging apparatus has been mainly described. However, various embodiments of the present invention is also applicable to an acoustic probe used for an ultrasonographic apparatus.

The present invention has been described in detail with reference to specific exemplary embodiments. However, the present invention is not limited to the above-described specific exemplary embodiments, and the exemplary embodiments can be modified within a range which does not depart from the technical spirit of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-129593, filed Jun. 30, 2017, which is hereby incorporated by reference herein in its entirety.

What is claimed is:

1. An acoustic probe comprising:
a plurality of transducers that receives acoustic waves; and
a supporting body including a supporting portion having a spherical surface which supports the plurality of transducers in a spiral array,
wherein a supporting position R at which the supporting portion supports the transducers is defined as $R(r_0, \theta, \varphi)$ [m, rad, rad] by a polar coordinate with respect to a center of the spherical surface by setting a sphere radius, a zenith angle, and an azimuth angle as "$r_0$", "$\theta$", and "$\varphi$",
wherein the plurality of transducers is arrayed at a certain azimuth angle spiral pitch in an azimuth angle direction of the spiral array and a certain axis direction spiral pitch in an axial direction of the spiral array, and wherein the azimuth angle spiral pitch is at an angle [rad] acquired by dividing $2\pi$ [rad] by 1+golden number, and
wherein the axis direction spiral pitch is parallel to a central axis direction of the spherical surface extending from the center to an extreme point.

2. The acoustic probe according to claim 1, wherein the azimuth angle spiral pitch coincides with an azimuth angle difference $\Delta\varphi$ between the two closest transducers to each other in a zenith angle $\theta$ direction.

3. The acoustic probe according to claim 1, wherein the axis direction spiral pitch coincides with a distance $\Delta z$ in the axis direction between the two closest transducers to each other in the zenith angle $\theta$ direction $$\Delta z = z_i - z_{i-1} = r_0(\cos\theta_i - \cos\theta_{i-1}) = r_0 \frac{\cos\theta_{N-1} - \cos\theta_0}{N-1}.$$

4. The acoustic probe according to claim 1, wherein the supporting portion supports the plurality of transducers to form only one spiral array.

5. The acoustic probe according to claim 1, wherein the spiral array is a Fibonacci array.

6. The acoustic probe according to claim 1, wherein, of the plurality of transducers, a starting point of the spiral array having a greatest zenith angle $\theta$ has a zenith angle $\theta$ of $8\pi/9$ [rad] or more and $\pi$ [rad] or less.

7. The acoustic probe according to claim 6, wherein, of the plurality of transducers, an ending point of the spiral array having a smallest zenith angle $\theta$ has a zenith angle $\theta$ of $\pi/3$ [rad] or more and $3\pi/4$ [rad] or less.

8. The acoustic probe according to claim 1, wherein the transducers are piezo-type transducers having pyroelectric ceramics or capacitance-type transducers having cavities between electrodes.

9. The acoustic probe according to claim 1, further comprising a light irradiation portion configured to irradiate a test subject with light.

10. The acoustic probe according to claim 9, wherein the supporting portion supports the light irradiation portion at a position having a zenith angle greater than the zenith angle of the starting point.

11. The acoustic probe according to claim 9, wherein the light irradiation portions are arranged on the supporting portion with uniform dispersibility.

12. The acoustic probe according to claim 11, wherein a spiral array of the plurality of light irradiation portions has an azimuth angle spiral pitch $2\pi/(1+\Psi)$ which is in common with the pitch of the spiral array of the plurality of transducers.

13. The acoustic probe according to claim 11,
wherein the supporting portion supports the plurality of light irradiation portions in a spiral array that satisfies the following expressions $$\phi_j = \frac{\pm 2\pi j}{1+\Psi} + \xi,$$

$$\Psi = \frac{1+\sqrt{5}}{2}, \text{ and}$$

$$\theta_j = \cos^{-1}\left[\cos\theta_0 + \frac{\cos\theta_{M-1} - \cos\theta_0}{M-1}j\right],$$

wherein "M" represents a number of light irradiation portions, "j" represents an array number (0, 1, . . . , M−1) assigned from 0 to each transducer by designating a side having "π" of the zenith angle θ as a starting point, and "ξ" represents an azimuth angle difference between a starting point of an array of the light irradiation portions and a starting point of an array of the transducers.

14. The acoustic probe according to claim 2, further comprising a camera having an imaging field facing toward the test subject at a position having a zenith angle greater than the zenith angle of the starting point.

15. The acoustic probe according to claim 2, further comprising a port for supplying or discharging an acoustic matching liquid at a position having a zenith angle greater than the zenith angle of the starting point.

16. An acoustic apparatus comprising:
the acoustic probe according to claim 1; and
a scanning unit configured to make the acoustic probe move in translation motion.

17. The acoustic apparatus according to claim 16 further comprising a light source optically connected to the light irradiation portion.

18. The acoustic apparatus according to claim 16, further comprising a signal processing unit configured to acquire information about a test subject based on a signal received by the acoustic probe.

19. The acoustic probe according to claim 1, wherein the symmetrical concave surface is an inner surface of a spherical cap.

20. The acoustic probe according to claim 1, wherein an axis of the spiral array coincides with an axis of the symmetrical concave surface.

21. An acoustic probe comprising:
a plurality of transducers that receive acoustic waves; and
a supporting body including a supporting portion having a symmetrical concave surface which supports the plurality of transducers,
wherein a supporting position R at which the supporting portion supports the transducers is defined as $R(r_0, \theta, \varphi)$ [m, rad, rad] by a polar coordinate with respect to a center of the symmetrical concave surface by setting a sphere radius, a zenith angle, and an azimuth angle as "$r_0$", "θ", and "φ",
wherein the supporting portion supports the transducers in a spiral array that satisfies the following expressions $$\Delta \phi = \phi_i - \phi_{i-1} = \frac{\pm 2\pi}{1+\Psi},$$

$$\Psi = \frac{1+\sqrt{5}}{2}, \text{ and}$$

$$\Delta z = z_i - z_{i-1} = r_0(\cos\theta_i - \cos\theta_{i-1}) = r_0 \frac{\cos\theta_{N-1} - \cos\theta_0}{N-1},$$

wherein "N" represents a number of transducers, "i" represents an array number (0, 1, . . . , N−1) assigned from 0 to each transducer by designating a side having "π" of the zenith angle θ as a starting point.

22. The acoustic probe according to claim 21, wherein the supporting portion supports the plurality of transducers to form only one spiral array.

23. The acoustic probe according to claim 21, wherein the spiral array is a Fibonacci array.

24. The acoustic probe according to claim 21, wherein, of the plurality of transducers, a starting point of the spiral array having a greatest zenith angle θ has a zenith angle θ of 8π/9 [rad] or more and π [rad] or less.

25. An acoustic probe comprising:
a plurality of transducers that receive acoustic waves; and
a supporting body including a supporting portion having a symmetrical concave surface which supports the plurality of transducers,
wherein a supporting position R at which the supporting portion supports the transducers is defined as $R(r_0, \theta, \varphi)$ [m, rad, rad] by a polar coordinate with respect to a center of the symmetrical concave surface by setting a sphere radius, a zenith angle, and an azimuth angle as "$r_0$", "θ", and "φ",
wherein the supporting portion supports the transducers in a spiral array that satisfies the following expressions $$\phi_i = \frac{\pm 2\pi i}{1+\Psi},$$

$$\Psi = \frac{1+\sqrt{5}}{2}, \text{ and}$$

$$\theta_i = \cos^{-1}\left[\cos\theta_0 + \frac{\cos\theta_{N-1} - \cos\theta_0}{N-1}i\right],$$

wherein "N" represents a number of transducers, "i" represents an array number (0, 1, . . . , N−1) assigned from 0 to each transducer by designating a side having "π" of the zenith angle θ as a starting point.

26. The acoustic probe according to claim 25, wherein the supporting portion supports the plurality of transducers to form only one spiral array.

27. The acoustic probe according to claim 25, wherein the spiral array is a Fibonacci array.

28. The acoustic probe according to claim 25, wherein, of the plurality of transducers, a starting point of the spiral array having a greatest zenith angle θ has a zenith angle θ of 8π/9 [rad] or more and π [rad] or less.

* * * * *